US00PP33719P2

(12) United States Plant Patent
Stoppel

(10) Patent No.: US PP33,719 P2
(45) Date of Patent: Dec. 7, 2021

(54) CHERRY TREE NAMED 'PRIM 25'

(50) Latin Name: ***Prunus avium* L.**
Varietal Denomination: Prim 25

(71) Applicant: Cerasina GmbH, Kressbronn (DE)

(72) Inventor: Peter Stoppel, Kressbronn (DE)

(73) Assignee: Cerasina GmbH, Kressbronn (DE)

( * ) Notice: Subject to any disclaimer, the term of this patent is extended or adjusted under 35 U.S.C. 154(b) by 0 days.

(21) Appl. No.: 17/165,150

(22) Filed: Feb. 2, 2021

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/085
See application file for complete search history.

*Primary Examiner* — Kent L Bell
(74) *Attorney, Agent, or Firm* — The Webb Law Firm

(57) ABSTRACT

A new and distinct variety of sweet cherry tree that produces dark red colored fruits with very firm fruit flesh.

4 Drawing Sheets

Botanical classification: *Prunus avium* L.
Varietal denomination: 'Prim 25'.

BACKGROUND OF THE INVENTION

The present invention comprises a new and distinct variety of sweet cherry tree, botanically known as *Prunus avium* L., and referred to by the varietal name 'Prim 25'. The new variety is the result of a planned breeding program in Kressbronn, Baden-Wuerttemberg, Germany between cherry tree variety named 'PC 7144-7', known and marketed as "Tieton" (female parent, U.S. Plant Pat. No. 8,051), and an unnamed and unpatented cherry tree variety as the male parent. The purpose of the breeding program was to produce high quality fruits. The new variety was first asexually reproduced via cuttings in Kressbronn, Baden-Wuerttemberg, Germany in 2006. The new variety has been trial and field tested and has been found to retain its distinctive characteristics and remain true to type through successive propagations. The present invention has not been evaluated under all possible environmental conditions. The phenotype may vary with variations in environment without a change in the genotype of the plant.

The new variety is similar to both parental varieties in exhibiting a dark red fruit color and high fruit firmness. The new variety differs from its parental varieties in tree habit, fruit ripening time, and fruit shape. A more detailed comparison to its male parent cannot be provided, as its exact identity is unknown. However, when specifically compared to "Tieton", 'Prim 25' has similar short stem lengths, fruit color, and S-alleles/S3S9, but exhibits a fruit ripening time that is 1 week earlier than "Tieton", a weaker growth habit than "Tieton", and fruit that is firmer than "Tieton". When compared to cherry tree variety named 'Burlat' (unpatented), the fruits of 'Prim 25' are much more firm than those of 'Burlat' and 'Prim 25' exhibits a weaker growth habit than 'Burlat'. Further, the following characteristics distinguish the new variety from other varieties known to the breeder:

1. 'Prim 25' exhibits a much darker fruit color than 'Bellise' (unpatented);
2. 'Prim 25' exhibits a fruit ripening time that is 8 days earlier than 'Grace Star' (unknown patent protection);
3. 'Prim 25' exhibits a flowering time that is 8 days earlier than 'Kordia' (unpatented), as well as shorter stem lengths than 'Kordia'; and
4. 'Prim 25' has a larger fruit size than 'PC 7146-23', aka "Chelan" (U.S. Plant Pat. No. 8,545).

DESCRIPTION OF THE DRAWINGS

The accompanying photographic drawings illustrate the new variety at approximately 7 years of age with the color being as nearly true as possible with color illustrations of this type.

DETAILED BOTANICAL DESCRIPTION

Figure 1:
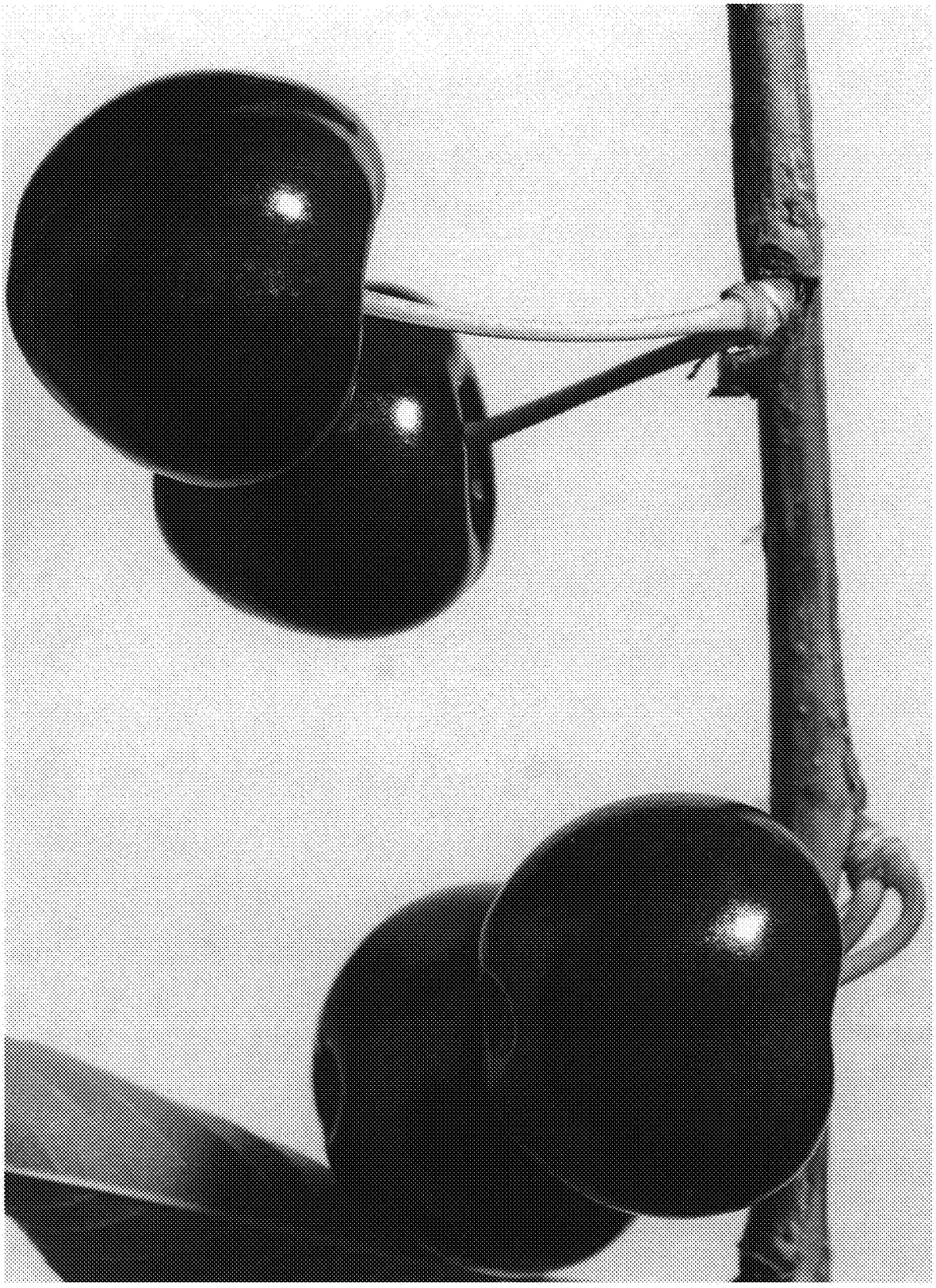
FIG. 1 is a close-up photograph of the fruit of 'Prim 25'.
Figure 2:
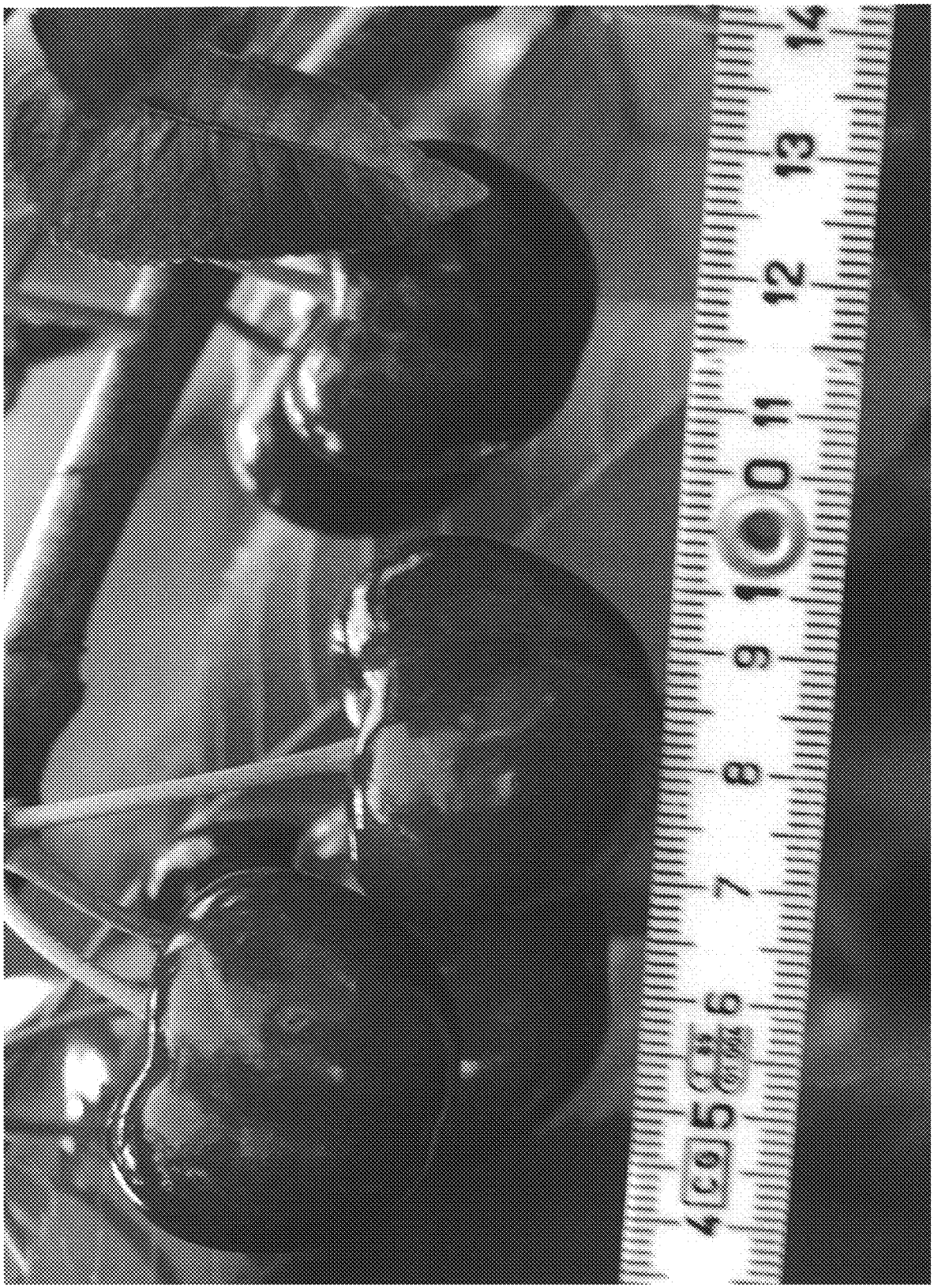
FIG. 2 is a close-up photograph of the fruit of 'Prim 25'.
Figure 3:
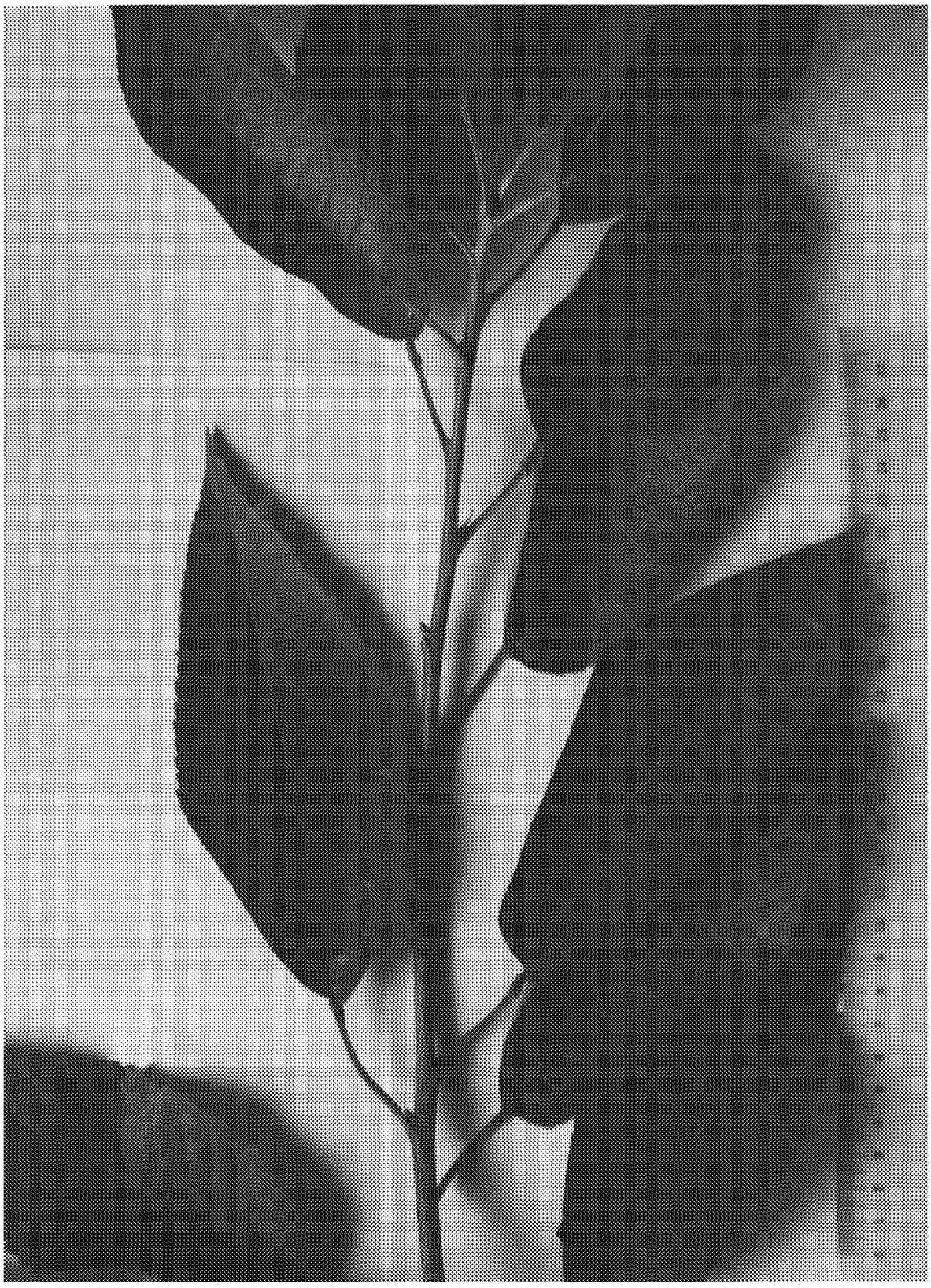
FIG. 3 is a close-up photograph of the leaves of 'Prim 25'.
Figure 4:
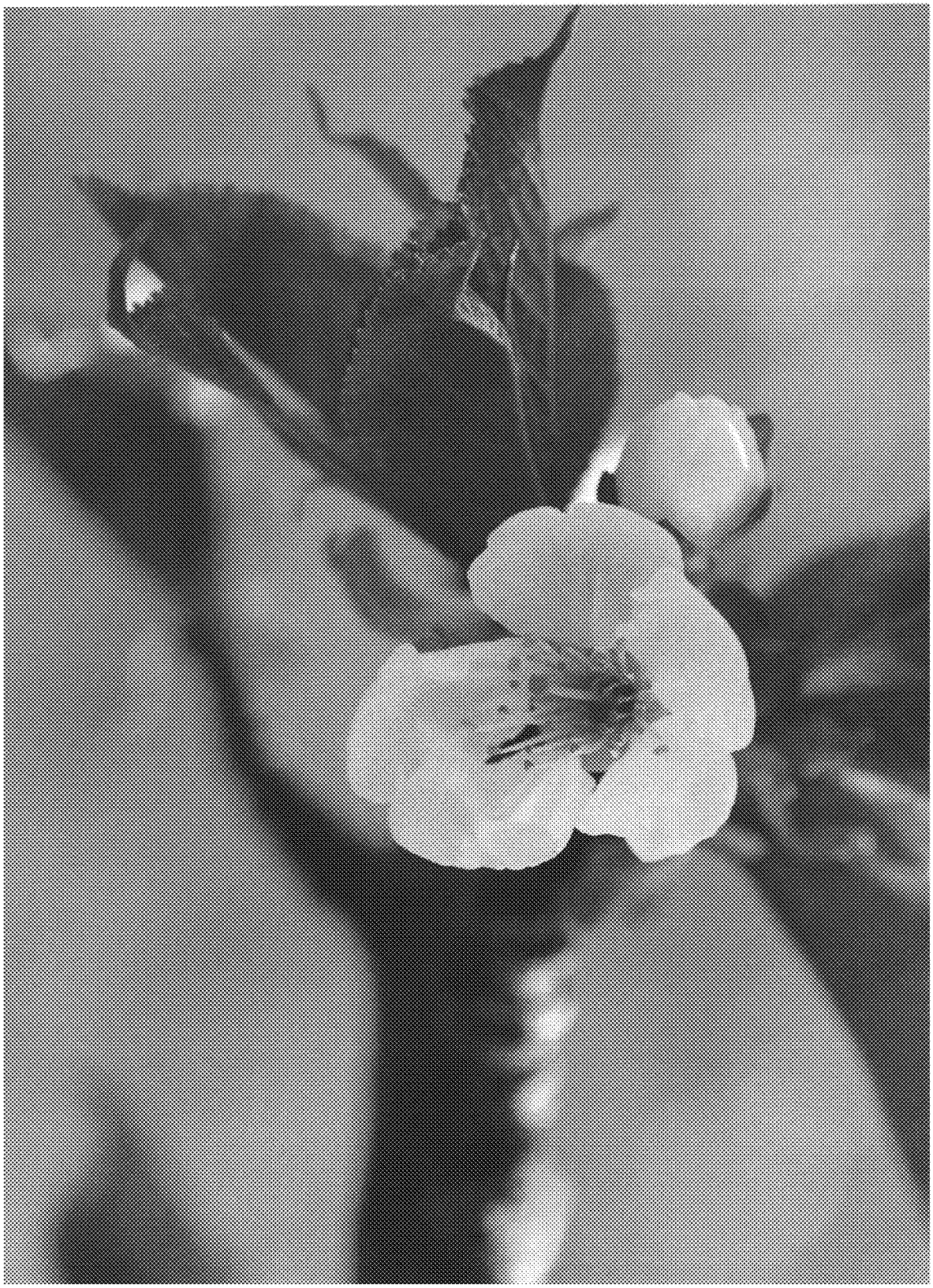
FIG. 4 is a close-up photograph of an open flower of 'Prim 25'.

The following detailed description sets forth the characteristics of the new variety. The data which defines these characteristics was collected by asexual reproductions via cuttings carried out in Kressbronn, Baden-Wuerttemberg, Germany. The new variety was grown outside under natural soil conditions. The color readings were taken outside in natural daylight and the variety was approximately 7 years old when described. Color references are primarily to The R.H.S. Colour Chart of The Royal Horticultural Society of London, except where terms of ordinary significance are used.

TREE

Height: 3.0 m.
Width: 2.0 m, measured at 10.0 cm above ground level.

Vigor: Medium.
Density: Medium.
Form: Upright spread with a medium level of lateral branching.
Growth type: Spreading.
Bearing: Annually on spurs, with 3-4 bud positions located at the base of one-year old shoots.
Disease/pest resistance or susceptibility: Nothing unusual noted to date.
Trunk:
*Size*.—Medium.
*Bark color*.—RHS 199A.
*Surface texture*.—Smooth, with prominent lenticels.
*Lenticels*.—Length: 1.0-2.0 cm. Width: 0.5 cm. Density: Medium. Color: RHS 167A.
Branches (at 1 year of age):
*Diameter*.—0.5-1.0 cm.
*Surface texture*.—Smooth, with lenticels present.
*Color*.—RHS 151C.
*Form*.—Of a typical sweet cherry tree.
*Average angle*.—40-55 degrees.
*Bud arrangement*.—Of a typical sweet cherry tree.
*Average internode length*.—3.5 cm.
*Lenticels*.—Length: About 1.0 mm. Width: About 1.0 mm. Shape: Rounded. Density: Few and scattered. Color: RHS 161B.
Leaves:
*Length*.—13.0-15.0 cm.
*Width*.—5.5-7.5 cm.
*Form*.—Elongated, round, and small.
*Shape*.—Elliptic to lanceolate.
*Texture*.—Leathery.
*Thickness*.—Medium.
*Apex*.—Acute.
*Base*.—Acute.
*Margin*.—Regularly serrate.
*Color*.—Upper surface: RHS 137A. Lower surface: RHS 139B.
*Petiole*.—Shape: Narrow. Length: 3.0-4.0 cm. Diameter: About 2.0 mm. Color: Adaxial surface: RHS 59A. Abaxial surface: RHS 149C. Venation: Type: Pinnate. Color: RHS 154D.

FLOWERS

Flower buds:
*Color*.—RHS 200B.
*Length*.—About 0.7 cm.
*Width*.—About 0.35 cm.
*Shape*.—Obtuse.
Flowers:
*Bloom timing*.—Toward the end of April in Kressbronn, Baden-Wuerttemberg, Germany.
*Blooming period*.—Medium to early in the season, similar to 'Burlat'.
*Number of flowers per raceme*.—3 to 7.
*Average flower diameter*.—42.0 mm.
*Pollination requirements*.—Cross-pollination needed.
*Petals*.—Number: 5 and slightly overlapping. Length: 18.0 mm. Width: 18.0 mm. Shape: Round. Apex: Slightly obcordate. Margin: Slightly undulate. Texture: Soft. Color: RHS 155D (both surfaces).
*Sepals*.—Length: 5.0-7.5 mm. Width: About 5.0 mm. Shape: Conical, with a bluntly pointed apex. Margin: Slightly undulate. Color: RHS 143C (both surfaces). Texture: Smooth.
Reproductive organs:
*Stamens*.—Number per flower: 28-35. Filament length: 5.0-14.0 mm.
*Anthers*.—Shape: Kidney. Length: 0.5 mm. Color: RHS 13B.
*Pollen*.—Color: RHS 13B. Amount: Plentiful.
*Pistil length*.—12.0 mm.
*Style*.—Length: 4.0-6.0 mm. Color: RHS 143C.
*Stigma*.—Shape: Oval. Color: Green.

FRUIT

Fruit:
*Maturity when described*.—Eating maturity.
*Shape*.—Long and heart-shaped.
*Weight per fruit*.—About 11.6 g.
*Flavor*.—Sweet and juicy with a pleasant aroma.
*Keeping quality of picked fruit*.—Good, especially in cold storage.
*Amount of fruit produced per tree*.—About 9.7 kg for five-year old trees.
*Size*.—Diameter: 2.8 cm. Length: 3.2 cm.
*Skin*.—Thickness: Medium. Texture: Smooth. Tendency to crack: Not prone to cracking from rain. Color: RHS 187A.
*Flesh*.—Aroma: Pleasant. Color: RHS 181A. Texture: Very firm. Eating quality: Good.
*Seeds*.—Number per fruit: 1. Length: 1.3 cm. Breadth: 0.9 cm. Form: Oval to rounded. Color: RHS N167A.
*Stem*.—Length: 3.5 cm. Width: 0.1 cm. Color: RHS 137C.

I claim:

1. A new and distinct variety of cherry tree, as is herein illustrated and described.

* * * * *